United States Patent [19]

Udovich et al.

[11] 4,416,802

[45] Nov. 22, 1983

[54] CATALYSTS FOR THE PRODUCTION OF MALEIC ANHYDRIDE BY THE OXIDATION OF BUTANE

[75] Inventors: Carl A. Udovich, Joliet; Robert C. Edwards, Naperville, both of Ill.

[73] Assignee: Standard Oil Co. (Indiana), Chicago, Ill.

[21] Appl. No.: 382,180

[22] Filed: May 26, 1982

[51] Int. Cl.$^3$ .............................................. B01J 27/14
[52] U.S. Cl. .................................. 502/209; 502/208; 549/259
[58] Field of Search ............................... 252/435, 437

[56] References Cited

U.S. PATENT DOCUMENTS

| | | | |
|---|---|---|---|
| 3,293,268 | 12/1968 | Bergman et al. | 252/437 X |
| 3,385,796 | 5/1969 | Kerr | 252/437 |
| 3,474,041 | 10/1969 | Kerr | 252/437 X |
| 3,832,359 | 8/1974 | Freerks et al. | 252/437 X |
| 3,864,280 | 2/1975 | Schneider | 252/435 |
| 3,867,411 | 2/1975 | Roffelson et al. | 252/437 X |
| 3,888,886 | 6/1975 | Young et al. | 252/437 X |
| 3,985,775 | 10/1976 | Harrison | 252/437 X |
| 4,016,105 | 4/1977 | Kerr | 252/437 |
| 4,147,661 | 4/1979 | Higgins et al. | 252/437 X |
| 4,149,992 | 4/1979 | Mount et al. | 252/437 X |
| 4,151,116 | 4/1979 | McDermott | 252/437 X |
| 4,251,390 | 2/1981 | Barone | 252/435 |
| 4,283,288 | 8/1981 | Udovich et al. | 252/437 |

*Primary Examiner*—William G. Wright
*Attorney, Agent, or Firm*—Gunar J. Blumberg; William T. McClain; William H. Magidson

[57] ABSTRACT

A process for the manufacture of a phosphorus/vanadium/metal oxide catalyst suitable for the oxidation of butane to maleic anhydride can be prepared by reacting in an aqueous medium a vanadium compound, inorganic acid and metal oxide, then adding orthophosphoric acid to form a soluble vanadium phosphorus metal oxide catalyst, removing the acidified water and adding an aliphatic alcohol, removing the alcohol and recovering under vacuum the solid phosphorus vanadium metal oxide catalyst.

8 Claims, No Drawings

CATALYSTS FOR THE PRODUCTION OF MALEIC ANHYDRIDE BY THE OXIDATION OF BUTANE

BACKGROUND OF THE INVENTION

1. Field of the Invention

The field of this invention relates to processes for the manufacture of phosphorus, vanadium and cometal catalysts suitable for the oxidation of butane to maleic anhydride.

2. Background

Maleic anhydride is of significant commercial interest throughout the world and is extensively used in the manufacture of alkyd resins. It is also a versatile intermediate for chemical synthesis. Consequently, large quantities of maleic anhydride are produced each year to satisfy these needs. The production of maleic anhydride by the catalytic oxidation of benzene and butene is well known, and until recently the prinicipal method employed for the manufacture of maleic anhydride was by the air oxidation of benzene in the presence of certain heavy metal oxide catalysts. However, because of the inherent toxicity of benzene fumes, the trend has been to eliminate the utilization of benzene as a feedback and newer facilities tend to utilize butane oxidation processes.

In general, catalysts proposed for the oxidation of butane to maleic anhydride have been based upon vanadium and phosphorus. In U.S. Pat. No. 3,293,268 it is disclosed that the oxidation of butane to maleic anhydride can be performed in the presence of a phosphorus-vanadium-oxygen containing complex catalyst. Though this catalyst is capable of oxidizing butane, it does not give sufficiently high yields. Yields of maleic anhydride of only 30 to 50 weight percent are reported. Various activators, stabilizers and promoters have been disclosed in the prior art to improve the yields of maleic anhydride. References include U.S. Pat. Nos. 3,867,411; 3,832,359; 3,888,886; 4,002,650; 4,147,661; 4,149,992; 4,151,116; 4,152,338; 4,152,339; and British application No. 2,019,839A. While the aforementioned prior art tends to bring about some improvement in the performance of the phosphorus vanadium catalyst there remains much room for improvement, particularly from the standpoint of high conversion, yield and catalyst life.

The object of the present invention is to provide a nonprecipitated method for the manufacture of phosphorus, vanadium and co-metal oxide catalysts by carrying out the reaction in both aqueous and non-aqueous solvents. A further object is to provide a process for the manufacture of maleic anhydride in the presence of the catalyst manufactured by the novel process.

Our catalyst is suitably prepared in aqueous solvents using inorganic acids and metal oxides such as molybdenum oxide, zinc oxide, uranium oxide, tungsten oxide, tin oxide, and bismuth oxide. When the aqueous solution is clear and substantial reduction of vanadium (V) to vanadium (IV) has taken place, phosphoric acid, such as 85 percent orthophosphoric acid, is added to form a soluble aqueous vanadium phosphorus metal oxide catalyst. A large quantity of water-hydrogen chloride is removed from the catalyst solution giving a thick syrup which is then diluted in methanol or other suitable alcohols; o-xylene can be added and the solution is refluxed. The alcohol, such as methanol, and o-xylene if present, is removed yielding a syrup which is dried to form the solid vanadium/phosphorus/metal oxide catalyst.

Our catalyst preparation proceeds according to the following reaction sequence:

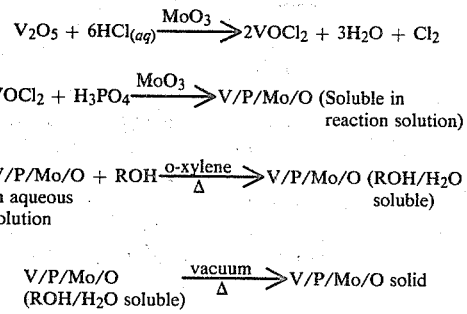

In place of HCl, other acids capable of reducing vanadium can be utilized. In place of molybdenum other metals such as tungsten, zinc, uranium, chromium, and tin can be used in our process. Our catalyst has a much higher activity than catalysts of the prior art, such as those disclosed in U.S. Pat. No. 3,862,146, and U.S. Pat. No. 4,328,126. Our process recovers 100 percent of the vanadium feedstock compared to the usual precipitative process which recovers only about 60 percent of the vanadium. Among the many advantages of our novel process for the manufacture of the catalyst can be cited the quantitative use of the expensive vanadium and the use of very cheap solvents such as water and methanol or ethanol and phosphoric acid.

The novel catalyst comprises a phosphorus vanadium mixed oxide promoted by metals. The atomic ratio of the vanadium to phosphorus can suitably be in the range of 0.5:1 to 1.25:1.0. The total atomic ratio of co-metal to vanadium advantageously is in the range of 0.75:1 to 1:1. It is preferred that the total atomic ratio of molybdenum to vanadium should be in the range of 0.001:1 to 0.2:1. The atomic ratio of phosphorus to vanadium is suitably in the range of 0.8:1 to 2:1, preferably 1:1 to 1.5:1.

The co-metal, such as molybdenum, may be added as a compound together with vanadium or separately introduced into the solution. Suitable molybdenum compounds comprise molybdenum oxide and most soluble molybdenum salts. If it is desired to improve physical properties of the catalysts they may be treated with the suspension of an inert support, for example, alumina, titania, silicon carbide, kieselguhr, pumice, or silica. The catalyst may be reinforced with such materials at any stage in its preparation.

According to our process, the average valence of vanadium is in the range of about 3.8 to 4.2. In our catalyst preparation, various anhydrous phosphoric acids may be used including ortho-phosphoric, pyrophosphoric, triphosphoric acid or meta-phosphoric acid. The vanadium compound can be vanadium pentoxide, vanadium tetrachloride, vanadium trichloride, vanadium oxydichloride, vanadium oxytrichloride, vanadium tetraoxide, vanadium oxalate, and most soluble vanadium complexes. Suitable vanadium compounds include: vanadium oxides such as vanadium pentoxide, vanadium trioxide and the like; vanadium oxyhalides such as vanadyl chloride, vanadyl dichloride, vanadyl trichloride, vanadyl bromide, vanadyl dibromide, vanadyl tribromide and the like; vanadium containing acids such as meta-vanadic acid, pyrovanadic acid and the like; vanadium salts such as ammonium meta-vanadate, vanadium sulfate, vanadium phosphate, vanadyl formate, vanadyl oxalate and the like. However, vanadium pentoxide is preferred.

This invention also comprises a process for oxidizing butane to maleic anhydride by contacting it in the presence of oxygen with the novel catalyst. The oxidation of butane to maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feedstream to the oxidation reactors will normally contain air and about 0.2 to about 1.7 mole percent of n-butane. About 0.8 to 1.5 mole percent of n-butane is satisfactory for optimum yield of maleic anhydride for the process of this invention. Although higher concentrations may be employed, explosive hazards may be encountered. Lower concentrations of butane, less than about one percent, of course, will reduce the total yield obtained at equivalent flow rates and, thus, are not normally economically employed. The flow rate of the gaseous stream through the reactor may be varied within rather wide limits, but preferred range of operations is at the rate of about 100 to 4000 cc of feed per cc of catalyst per hour and more preferably about 1000 to 2400 cc of feed per cc of catalyst per hour. Residence times of the gas stream will normally be less than about four seconds, more preferably less than about one second, and down to a rate where less efficient operations are obtained. The flow rates and residence times are calculated at standard conditions of 760 mm of mercury and at 25° C. A variety of reactors will be found to be useful and multiple tube heat exchanger type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium to conduct heat from the reactors such as lead and the like, but it has been found that eutectic salt baths are completely satisfactory. One such salt bath is a sodium nitrate, sodium nitrite-potassium nitrate eutectic constant temperature mixture. An additional method of temperature control is to use a metal block reactor whereby the metals surrounding the tube act as a temperature regulating body. As will be recognized by a man skilled in the art, the heat exchanger medium may be kept at the proper temperature by heat exchangers and the like. The reactor or reaction tubes may be iron, stainless steel, carbon steel, nickel, glass tubes such as vycor and the like. Both carbon steel and nickel tubes have excellent long life under the conditions of the reaction described herein. Normally, the reactors contain a preheat zone under an inert material such as one-quarter inch Alundum pellets, inert ceramic balls, nickel balls, or chips and the like present at about one-half to one-tenth the volume of the active catalyst present.

The temperature of reaction may be varied within some limits but, normally the reaction should be conducted at a temperature within the rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than 20°–50° F. above the salt bath temperature. The temperature of the reactor, of course, will also depend to some extent upon the size of the reactor and the butane concentration.

The reaction may be conducted at atmospheric, superatmospheric, or below atmospheric pressure. The exit pressure will be at least slightly higher than the ambient pressure to insure a positive flow from the reaction. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride. The following examples will serve to provide a fuller understanding of the invention, but it is to be understood that these examples are given for illustrative purposes only and will not be interpreted as limiting the invention in any way. In the examples the terms "conversion", "selectivity" and "yield" are defined as follows:

$$\text{Conversion \%} = \frac{\text{Moles hydrocarbon reacted}}{\text{Moles hydrocarbon in feed}} \times 100$$

$$\text{Selectivity \%} = \frac{\text{Moles maleic produced}}{\text{Moles hydrocarbon feed consumed}} \times 100$$

$$\text{Yield Wt. \%} = (\text{Conversion}) \times (\text{Selectivity}) \times 169$$

EXAMPLE 1

Vanadium pentoxide, 91 g (0.5 mole), 1.5 l of 38 percent hydrochloric acid, and 4.4 g (0.03 mole) of molybdenum trioxide were added to a 3-l 3-neck round bottom flask equipped with a mechanical stirrer, reflux condenser, thermometer, and heated with an electrical mantle. The solution at this time was red-brown in color. The solution was refluxed for 2 hrs. at a temperature of 108° C.; the color changing from red-brown, to blue-green to blue during the reflux. At this time 148 g (1.28 mole) of 85 percent $H_3PO_4$ was added to the solution and distillation of $H_2O$-HCl was started using a side arm. A small amount of solids was observed in the reaction flask. The distillation was stopped, the contents filtered, and the distillation resumed. After 1200 ml of $H_2O$-HCl were removed, the distillation was terminated leaving a viscous blue syrup in the flask.

Approximately one-half of this syrup was dissolved in 400 ml of methanol. This solution was placed in a 1-l 1-neck round bottom flask equipped with a reflux condenser, stirring bar, electric mantle, and placed on a hot plate stirrer. O-xylene, 150 ml, was added to the solution which was then refluxed for 5.5 hrs. This solution was distilled until a viscous blue syrup covered with a layer of o-xylene was present. The o-xylene was decanted from the syrup, the syrup was placed in a plastic beaker, and it was dried in a vacuum oven (18–20 in. Hg vacuum) overnight at 115°–120° C. with a small nitrogen purge passing through the oven. A small dark-brown crust which covered the blue catalyst was removed mechanically.

EXAMPLE 2

The catalyst prepared in example one was crushed, combined with 5 percent by weight of graphite, and tableted into cored 3/16"pellets having a 5 lb. crush strength. Analysis of this catalyst by X-ray diffraction gave 72 percent phase A and 16 percent VO(H$_2$PO$_4$)$_2$. A 6 cm$^3$ load of this catalyst (bulk density=0.9 g/cm$^3$) was placed in a minireactor under a 1.05 percent butane-synthetic air mixture and brought on stream as follows:

| | |
|---|---|
| 0-350° F. | 1.5 hrs. |
| 350° F. | 2 hrs. |
| 350-780° F. | 2 hrs. |
| 780° F. | Overnight |
| 830° F. | Next Day |

The space velocity of feed over this catalyst was 1200 hr$^{-1}$. The performance data for this catalyst are shown in Table I.

TABLE I

Performance Data for Catalyst in Example 2.

| Days on Stream | Temperature, °F. | Conversion, Mole % | Selectivity Mole % | Yield Wt. % |
|---|---|---|---|---|
| 5 | 830 | 81 | 65 | 89 |
| 29 | 804 | 82 | 67 | 93 |
| 58 | 790 | 87 | 65 | 96 |
| 104 | 770 | 88 | 63 | 94 |
| 170 | 776 | 88 | 63 | 94 |

EXAMPLE 3

The remainder of the aqueous syrup from Example 1 was dried in a vacuum oven (18-20 in Hg vacuum) overnight at 115°-120° C. with a small nitrogen purge passing through the oven. This blue-green catalyst was crushed, combined with 5 percent by weight of graphite, and tableted into cored 3/16" pellets having a 5.5 lb. crush strength. The X-ray diffraction analysis of this catalyst have 61 percent phase A and 16 percent VO(H$_2$PO$_4$)$_2$. A 6 cm$^3$ loading of this catalyst was placed in a minireactor under a 1.05 percent n-butane in synthetic air mixture and brought on stream in a similar manner to Example 2. This catalyst when evaluated at a feed space velocity of 1200 hr$^{-1}$ gave a best performance of 73 mole percent conversion, 63 mole percent selectivity, and 78 weight percent maleic anhydride yield after 49 days on stream at 831° F. This demonstrates the importance of treating the aqueous syrup with methanol or other suitable solvents.

EXAMPLE 4

Using the same experimental set up as described in Example 1, 91 g of vanadium pentoxide (0.5 mole), 1.5 l of 38 percent hydrochloric acid, and 4.4 g (0.03 mole) of molybdenum trioxide were refluxed for 2 hours and 20 minutes. The color changed from red-brown to blue during reflux indicating a substantial amount of reduction of vanadium (V) to vanadium (IV). After the addition of 148 g of 85 percent orthophosphoric acid, the solution was filtered. Then 1150 mls. of hydrochloric acid-water were removed by distillation causing the temperature of the blue reaction solution to increase from 112° C. to 120° C. Isopropyl alcohol, 300 ml, and 75 ml of o-xylene were added to the blue syrup. The solution was refluxed for 1.5 hours followed by distillation of solvent until the temperature of the mixture reached 110° C. The viscous syrup was poured into a teflon dish and dried overnight in a vacuum oven at 120° C. and 18-20 in. of Hg vacuum with a small nitrogen purge flowing through the oven.

The dried catalyst was crushed, mixed with 5 percent graphite, and tableted into cored 3/16" pellets having a 7-8 lb. crush strength. An X-ray diffraction analysis of this catalyst precursor gave 63 percent phase A and 13 percent vanadyl bisdihydrogenphosphate. A 6 cm$^3$ loading of this catalyst was evaluated in a minireactor under a 1.05 percent n-butane in synthetic air mixture at a space velocity of 1200 hr$^{-1}$. After 29 days on stream, this catalyst gave 80 mole percent conversion, 63 mole percent selectivity, and 85 weight percent maleic anhydride yield at 832° F.

EXAMPLE 5

Using the previously described experimental set up, 91 g of vanadium pentoxide (0.5 mole), 1.5 l of 38 percent hydrochloric acid, and 8.58 g of uranium trioxide (0.03 mole) were refluxed at 112° C. for 4 hours. Again the color changed from red-brown to green to blue. After the addition of 148 g of 85 percent orthophosphoric acid (1.28 mole), hydrochloric acid-water was removed by distillation until the temperature of the blue syrup reached 123° C. After the syrup cooled to 70° C., one liter of methanol and 300 ml of o-xylene were added to the syrup and the mixture was refluxed for 2.5 hours at 70° C. Solvent was then removed by distillation until the temperature of the solution reached 95° C. The syrup was poured into a teflon dish and dried in a vacuum oven overnight at 120°-125° C. and 2-3 in. of Hg vacuum with a small nitrogen purge passing over the catalyst.

The dried catalyst precursor was crushed, mixed with 5 percent graphite, and tableted into 3/16" cored pellets having a 5.9-7.0 lb. crush strength. X-ray diffraction analysis gave 73 percent phase A and 13 percent vanadyl bisdihydrogenphosphate. This catalyst (6 cm$^3$) was evaluated in minireactor under 1.05 percent n-butane in synthetic air at a space velocity of 1200 hr$^{-1}$. Its performance after 98 days on stream was 79 mole percent conversion, 63 mole percent selectivity, and 84 weight percent yield of maleic anhydride at 829° F.

EXAMPLE 6

Using the same experimental set up, 91 g of vanadium pentoxide (0.5 mole), 1.5 l of 38 percent hydrochloric acid, and 4.4 g of molybdenum trioxide (0.03 mole) were refluxed at 112° C. for 2½ hours. At this time, 148 g of 85 percent orthophosphoric acid (1.28 mole) were added to the reaction solution. Hydrochloric acid-water (about 1225 mls) was removed until the reaction solution reached 128.5° C. When the solution cooled to 75° C., 1 l of methanol and 300 ml of o-xylene were added and the solution was refluxed for 24 hours. After 18 hours of reflux, light blue precipitate was observed in the solution. Approximately 500 ml of solvent were removed by distillation. The contents of the flask were poured into a 1 l beaker placed in a vacuum oven to dry overnight at 10-15 in. Hg vacuum and 120°-130° C. with a small nitrogen purge passing through the oven.

The dry catalyst precursor was crushed, mixed with 5 percent graphite, and formed into cored 3/16" pellets having a 6-6.5 lb. crush strength. The X-ray diffraction analysis of the catalyst precursor gave 81 percent phase A and no vanadyl bisdihydrogen-phosphate.

The catalyst (6 cm$^3$) was evaluated in a minireactor under 1.05 percent n-butane in synthetic air at a space velocity of 1200 hr$^{-1}$. Its performance is summarized in Table II.

TABLE II

| | Performance of Catalyst in Example 6 | | | |
|---|---|---|---|---|
| Days on Stream | Temperature, °F. | Conversion, Mole % | Selectivity, Mole % | yield, Wt. % |
| 5 | 780 | 62 | 67 | 70 |
| 11 | 802 | 85 | 65 | 93 |
| 39 | 814 | 86 | 66 | 95 |
| 52 | 792 | 88 | 63 | 93 |

EXAMPLE 7

Using the previously described experimental set up, 91 g vanadium pentoxide (0.5 mole), 1.5 l of 38 percent hydrochloric acid, and 4.4 g of molybdenum trioxide (0.03 mole) were refluxed for 3 hours at 112° C. Following this reflux, 138 g of 85 percent orthophosphoric acid (1.2 mole) were added to the blue solution and solvent was removed by distillation until the temperature of the solution reached 127° C. When the viscous solution cooled to 80° C., 250 ml of methanol were added and the solution was allowed to reflux for 15 hours at 75° C. After distilling off about 100 ml of solvent, the contents of the flask were poured into a teflon dish and placed in a vacuum oven overnight at 120°–130° C. and 10 in. of Hg vacuum with a small nitrogen purge passing through the oven.

The dried catalyst precursor was crushed, mixed with 5 percent graphite, and formed into 3/16" cored pellets having a 3 lb. crush strength. The X-ray diffraction analysis of this catalyst precursor gave 85 percent phase A and no vanadyl bishydrophosphate. The catalyst (6 cm$^3$) was evaluated in a minireactor under 1.05 percent n-butane in synthetic air at a space velocity of 1200 hr$^{-1}$. Its performance is documented in Table III. The excellent performance of this catalyst demonstrates that different catalyst P/V ratios are effective and that good catalysts can be prepared without using o-xylene, although the use of o-xylene is preferred for consistency in catalyst performance between repeat preparations.

TABLE III

| | Performance of Catalyst in Example 7 | | | |
|---|---|---|---|---|
| Days on Stream | Temperature, °F. | Conversion, Mole % | Selectivity, Mole % | Yield, Wt. % |
| 6 | 783 | 77 | 68 | 88 |
| 15 | 784 | 86 | 67 | 97 |
| 41 | 783 | 87 | 67 | 99 |
| 78 | 770 | 89 | 65 | 98 |

EXAMPLE 8

Using the standard set up described earlier, 91 g of vanadium pentoxide (0.05 mole), 1.5 l of 38 percent hydrochloric acid, and 4.4 g of molybdenum trioxide (0.03 mole) were refluxed for 3 hours at 112° C. At this time, 148 g of 85 percent orthophosphoric acid (1.28 mole) were added to the blue solution. Solvent was distilled until the temperature of the reaction solution reached 130° C. When the blue syrup cooled to 75° C., 250 ml of tetrahydrofuran were added to the syrup and the solution was refluxed for 17 hours. After about 14 hours some precipitate was noticed in the solution. After distilling off 100–200 ml of liquid, the contents of the flask were poured into a teflon dish and placed in a vacuum oven overnight at 120°–130° C. and 10 in. of Hg vacuum with a small nitrogen purge passing through the oven.

The dried catalyst precursor was crushed, mixed with 5 percent graphite and formed into 3/16" cored pellets having a 5.5–6 lb. crush strength. Analysis of the precursor by X-ray diffraction showed 77 percent phase A and 2 percent vanadyl bisdihydrogenphosphate. The catalyst (6 cm$^3$) was evaluated in a minireactor under 1.05 percent n-butane in synthetic air at a space velocity of 1200 hr$^{-1}$. After 25 days on stream, the catalyst performance was 81 mole percent conversion, 64 mole percent selectivity, and 88 weight percent yield of maleic anhydride. This example shows that solvents other than alcohols can be used to prepare good performing catalysts using this procedure, although methanol is preferred.

EXAMPLE 9

Using the standard reaction set up, 91 g of vanadium pentoxide (0.5 mole) and 0.5 l of 38 percent hydrochloric acid were refluxed for 10 minutes at 111° C. After the reaction solution was cooled to 80° C., 11.77 g of zinc metal (0.18 mole) were added slowly to the reaction solution. The solution was allowed to reflux for 1 hour before 138 g of 85 percent orthophosphoric acid (1.2 mole) was added. About 440 ml of solvent was distilled until the solution temperature reached 130° C. After the solution temperature decreased to 70° C., 400 ml of methanol and 100 ml of o-xylene were added to the dark blue solution and it was allowed to reflux for 20 hours. Solvent (295 ml) was removed by distillation and the syrup was poured into a teflon dish. The syrup was dried overnight in a vacuum oven at 140° C. and 10 in. of Hg vacuum with a small nitrogen purge passing through the oven.

The dried catalyst precursor was crushed, mixed with 5 percent Sterotex, and formed into 3/16" cored pellets having a 8–10 lb. crush strength. The catalyst (6 cm$^3$) was evaluated in a minireactor under a 1.05 percent n-butane in synthetic air mixture at a space velocity of 1200 hr$^{-1}$. After 56 days on stream, the catalyst gave a performance of 77 mole percent conversion, 63 mole percent selectivity, and 82 weight percent maleic anhydride yield at 828° F.

EXAMPLE 10

Using the standard experimental set up, 91 g of vanadium pentoxide, 1.5 l of 38 percent hydrochloric acid, and 6.96 g of tungsten trioxide (0.03 mole) were refluxed for 2.5 hours at 112° C. Following the addition of 138 g of 85 percent orthophosphoric acid (1.2 mole), solvent was removed by distillation until the temperature of the reaction solution reached 130° C. When the solution cooled to 70° C., 500 ml of methanol were added and the solution was refluxed for 16 hours. Solvent (200–300 ml) was removed by distillation and the blue syrup was poured into a teflon dish. The material was dried overnight in a vacuum oven at 120°–130° C. and 10 in. of Hg vacuum with a small purge of nitrogen passing through the oven.

The dried catalyst precursor was crushed, mixed with 5 percent Sterotex, and formed into 3/16" cored pellets having a 7–8.5 lb crush strength. The catalyst (6 cm$^3$) was evaluated in a minireactor under 1.05 percent n-butane in synthetic air at a space velocity of 1200 hr$^{-1}$. After 56 days on stream the performance of the catalyst was 82 mole percent conversion, 61 mole percent selectivity, and 84 weight percent yield of maleic anhydride at 817° F.

We claim:

1. A process for the manufacture of a phosphorus/vanadium/metal oxide catalyst suitable for use in the manufacture of maleic anhydride which process comprises reacting in an aqueous medium, a vanadium compound and inorganic acid and metal oxide, then adding orthophosphoric acid to form a soluble vanadium phosphorus metal oxide catalyst removing the acidified water and adding an aliphatic alcohol having 1 to 8 carbon atoms, removing the alcohol and drying the catalyst syrup under vacuum of about 0 to 300 mm Hg at a temperature of 90° to 120° C. to produce the solid catalyst.

2. The process of claim 1 wherein the vanadium compound is vanadium pentoxide.

3. The process of claim 2 wherein the alcohol is methanol and the inorganic acid is HCl and the orthophosphoric acid is 85 to 95 percent orthophosphoric acid.

4. The process of claim 3 wherein the vanadium compound is vanadium pentoxide.

5. A process for the manufacture of a phosphorus/vanadium/molybdenum oxide catalyst suitable for use in the manufacture of maleic anhydride which process comprises reacting in an aqueous medium vanadium compound and inorganic acid and molybdenum oxide, then adding orthophosphoric acid to form a soluble vanadium phosphorus molybdenum oxide catalyst, removing the acidified water and adding an aliphatic alcohol having 1 to 8 carbon atoms, removing the alcohol and drying the catalyst syrup under vacuum of about 0 to 300 mm Hg at a temperature of about 90° to 120° C. to produce the solid vanadium phosphorus molybdenum oxide catalyst.

6. The process of claim 4 wherein the alcohol is methanol.

7. The process of claim 6 wherein the inorganic acid is HCl.

8. The process of claim 7 wherein the orthophosphoric acid is 85 to 95 percent orthophosphoric acid.

* * * * *

UNITED STATES PATENT OFFICE
CERTIFICATE OF CORRECTION

Patent No. 4,416,802             Dated November 22, 1983

Inventor(s) Udovich, Carl A. - Edwards, Robert C.

It is certified that error appears in the above-identified patent and that said Letters Patent are hereby corrected as shown below:

Patent

| Column | Line  |                     |                              |
|--------|-------|---------------------|------------------------------|
| 1      | 9     | "cometal"           | should be -- co-metal --     |
| 1      | 26-27 | "feedback"          | should be -- feedstock --    |
| 1      | 42    | "application"       | should be -- Application --  |
| 3      | 66    | "within the rather" | should be -- within a rather -- |
| 5      | 42    | "catalyst have 61"  | should be -- catalyst gave 61 -- |
| 7      | 20    | "91 g vanadium"     | should be -- 91g of vanadium -- |

Signed and Sealed this

Twenty-eighth Day of May 1985

[SEAL]

Attest:

DONALD J. QUIGG

Attesting Officer  Acting Commissioner of Patents and Trademarks